US010105515B2

(12) United States Patent
Fasano et al.

(10) Patent No.: US 10,105,515 B2
(45) Date of Patent: Oct. 23, 2018

(54) CONTROL HANDLE FOR CATHETERS OR CANNULAS FOR MEDICAL USE

(71) Applicant: FIAB S.P.A., Vicchio (IT)

(72) Inventors: Antonio Fasano, Florence (IT); Alberto Calabro', Florence (IT); Stefano Piattoli, Pelago (IT)

(73) Assignee: FIAB S.P.A., Vicchio (IT)

( * ) Notice: Subject to any disclaimer, the term of this patent is extended or adjusted under 35 U.S.C. 154(b) by 917 days.

(21) Appl. No.: 14/509,389

(22) Filed: Oct. 8, 2014

(65) Prior Publication Data

US 2015/0141914 A1     May 21, 2015

(30) Foreign Application Priority Data

Nov. 19, 2013    (IT) ............................... FI2013A0277

(51) Int. Cl.
    *A61M 31/00*        (2006.01)
    *A61M 25/01*        (2006.01)
    (Continued)

(52) U.S. Cl.
    CPC ......... *A61M 25/0136* (2013.01); *A61B 34/70* (2016.02); *A61M 25/0113* (2013.01);
    (Continued)

(58) Field of Classification Search
    CPC .............. A61M 25/01; A61M 25/0136; A61M 25/0113; A61M 25/0905; A61M 25/09041; A61M 2025/09116; A61M 2025/09125
    (Continued)

(56) References Cited

U.S. PATENT DOCUMENTS 4,326,520 A     4/1982   Alley
5,159,861 A     11/1992   Anderson
(Continued)

FOREIGN PATENT DOCUMENTS

CN     201625315     11/2010
CN     202036662     11/2011
(Continued)

*Primary Examiner* — Kevin C Sirmons
*Assistant Examiner* — Tiffany Legette-Thompson
(74) *Attorney, Agent, or Firm* — Pearne & Gordon LLP

(57) ABSTRACT

A control handle (1) for a tubular element (100) for medical use, comprising an outer casing (2) comprising a first half-shell (2*a*) and a second half-shell (2*b*) connected to each other in a respective side connecting portion so that the first (2*a*) and the second (2*b*) half-shell are configurable in at least a configuration of being moved away from each other, adapted to enable the transversal insertion of at least a portion of the tubular element (100) between the two half-shells (2*a*, 2*b*), and a configuration of being moved near each other adapted to close over said portion of the tubular element (100). Each half-shell (2*a*, 2*b*) has a respective jaw (9*a*, 9*b*), the jaws (9*a*, 9*b*) of the two half-shells (2*a*, 2*b*) cooperate with each other to define a clamping member (9) suitable for being tightened around a portion of the tubular element (100).

A control handle (1) further comprising driving means (11), applied on at least one of said half-shells (2*a*, 2*b*) and acting upon the respective jaw (9*a*, 9*b*) to move said jaw (9*a*, 9*b*) away from and toward the other jaw (9*b*, 9*a*) so as to produce, respectively, a release configuration and a clamping configuration of said clamping member (9).

26 Claims, 6 Drawing Sheets

(51) Int. Cl.
 *A61B 34/00* (2016.01)
 *A61M 25/09* (2006.01)
 *A61B 17/00* (2006.01)

(52) U.S. Cl.
 CPC ............... *A61B 2017/0046* (2013.01); *A61B 2017/00318* (2013.01); *A61B 2017/00469* (2013.01); *A61M 2025/09116* (2013.01)

(58) Field of Classification Search
 USPC ..................................................... 604/95.01
 See application file for complete search history.

(56) References Cited

U.S. PATENT DOCUMENTS

| | | | |
|---|---|---|---|
| 5,971,991 | A | 10/1999 | Sunderland |
| 6,533,772 | B1 * | 3/2003 | Sherts ............... A61M 25/0113 279/42 |
| 2008/0262432 | A1 | 10/2008 | Miller |
| 2009/0082722 | A1 | 3/2009 | Munger et al. |
| 2013/0150820 | A1 * | 6/2013 | Cappello ............... A61M 5/30 604/500 |
| 2013/0184684 | A1 * | 7/2013 | Yardley ................ A61F 13/126 604/514 |
| 2014/0039465 | A1 * | 2/2014 | Schulz ............... A61M 25/0113 604/528 |

FOREIGN PATENT DOCUMENTS

| | | | |
|---|---|---|---|
| EP | 2497521 | | 9/2012 |
| EP | 2497521 A1 * | 9/2012 | ........ A61M 25/0113 |

* cited by examiner

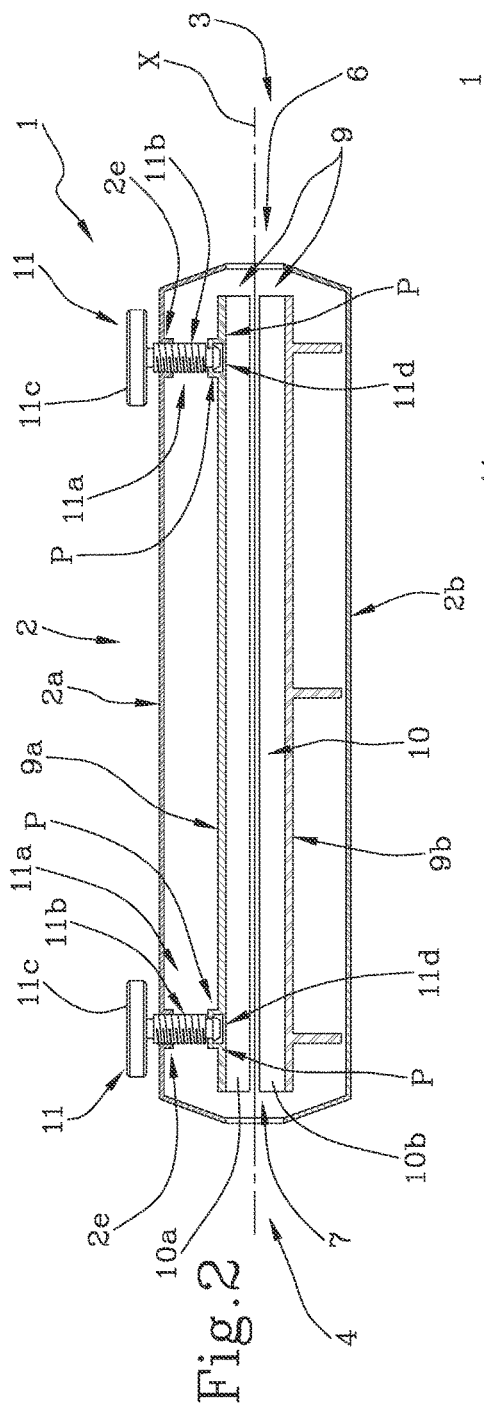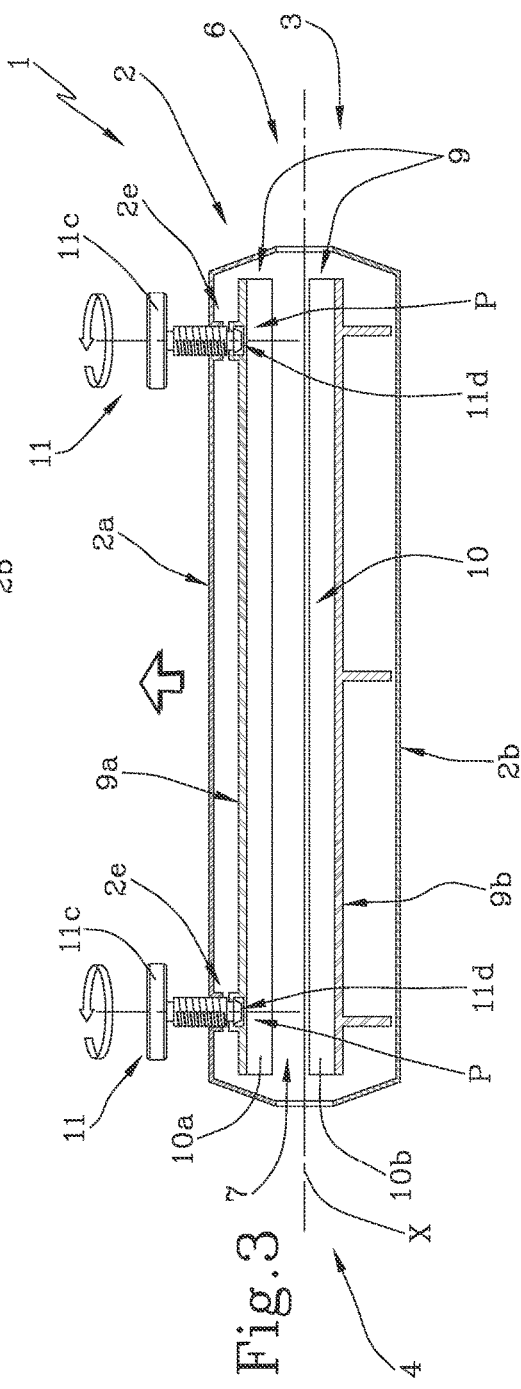

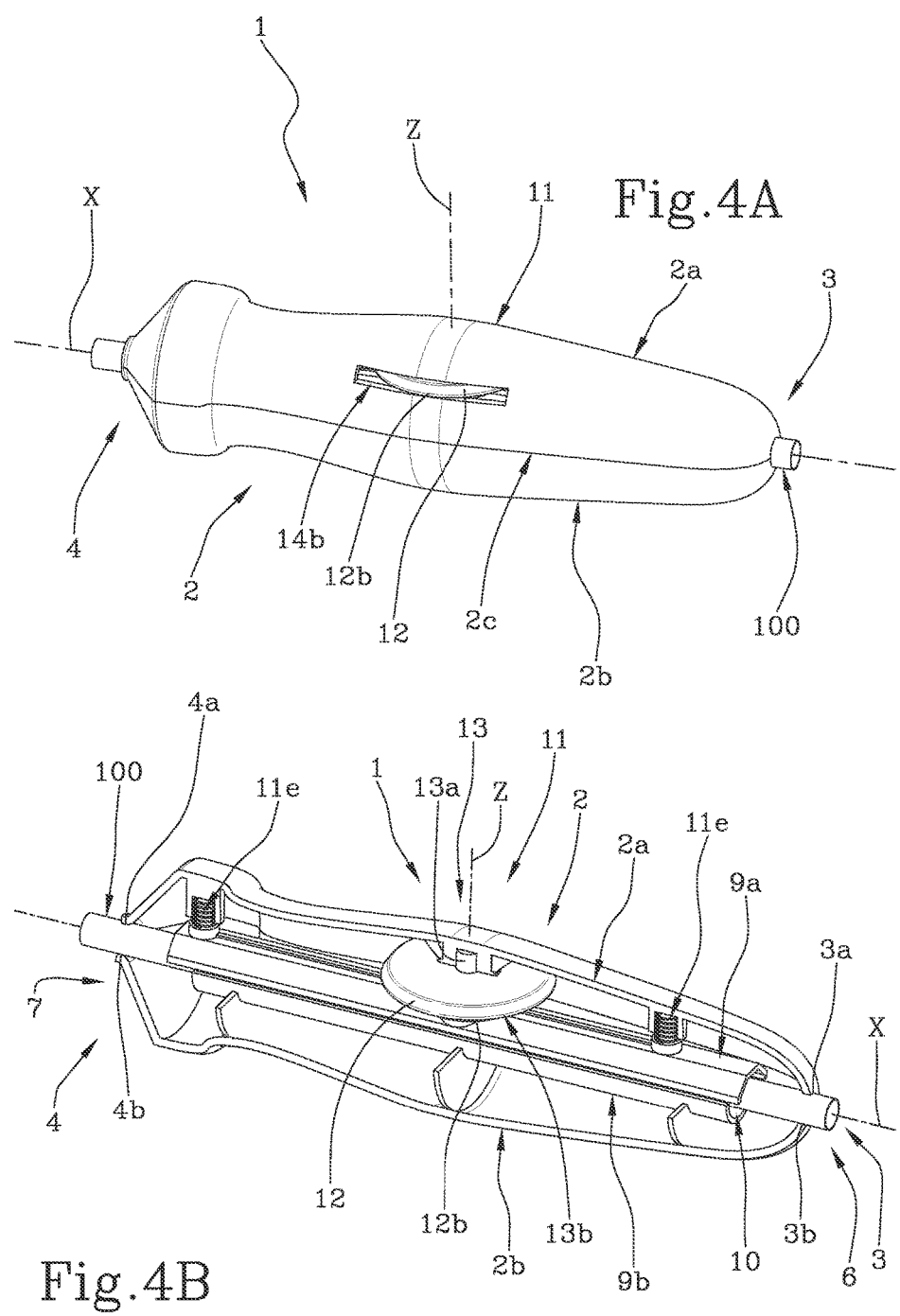

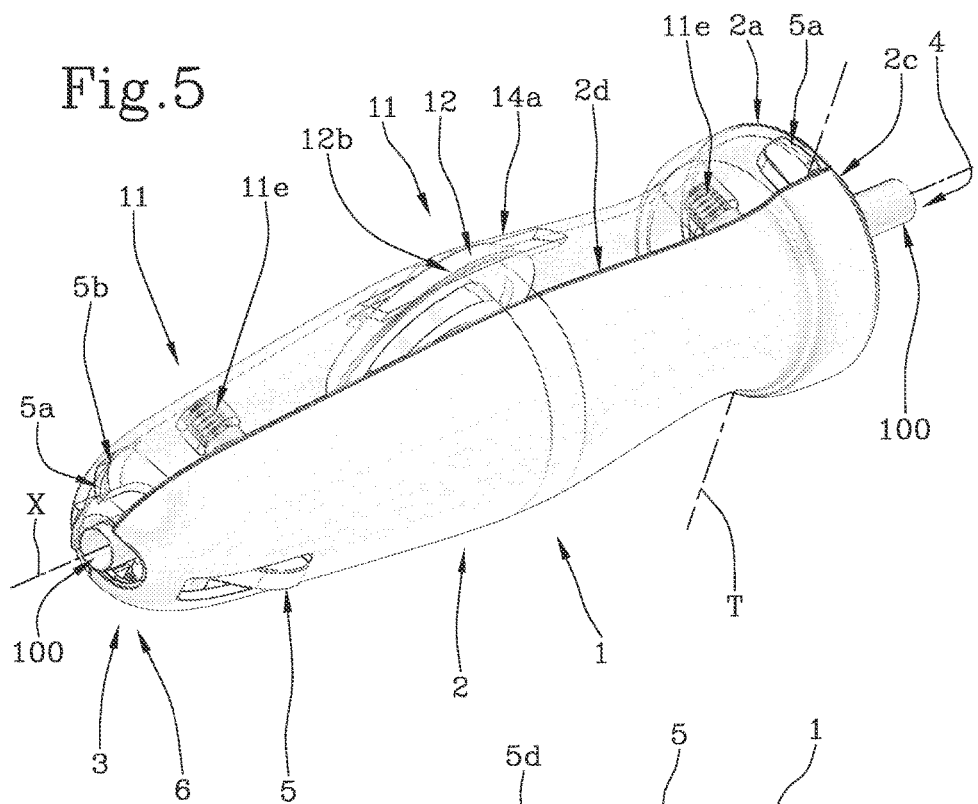
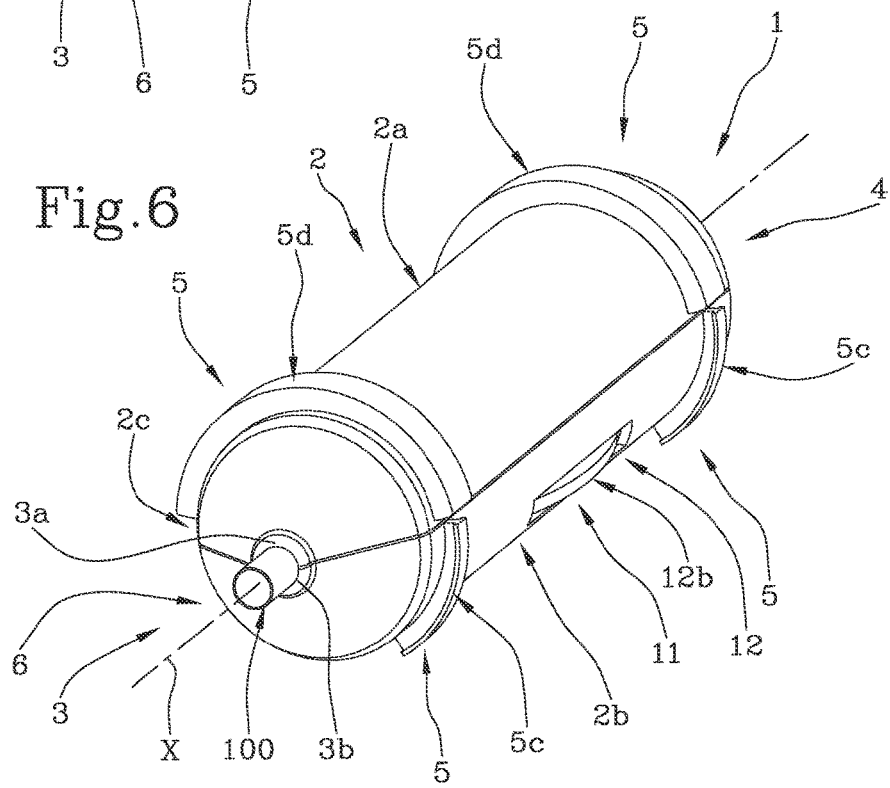

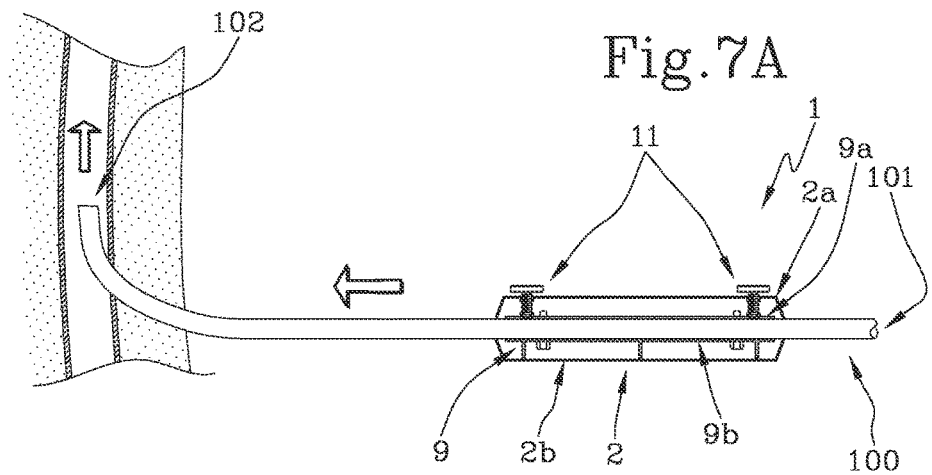
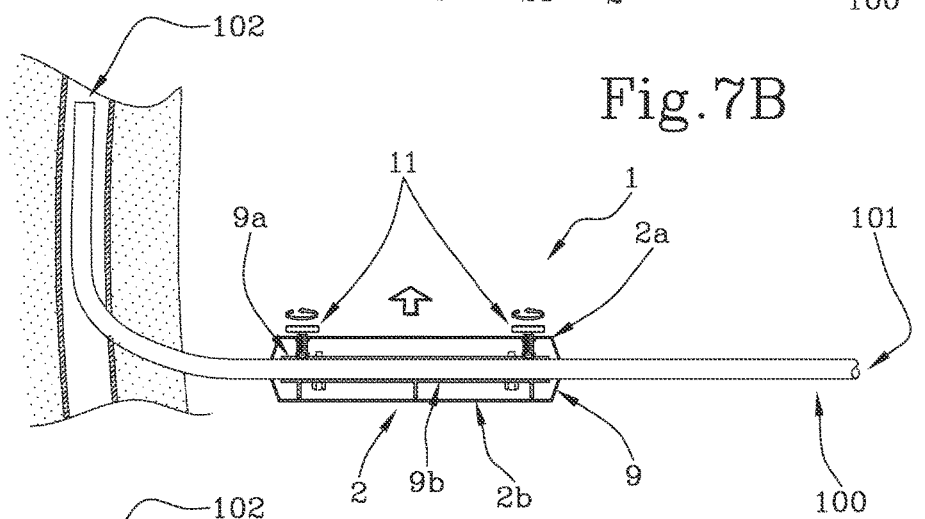
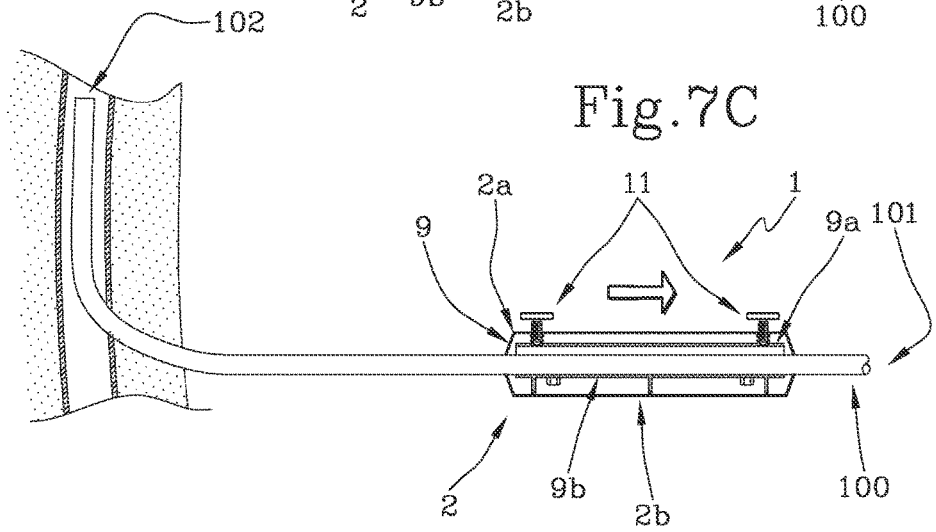

CONTROL HANDLE FOR CATHETERS OR CANNULAS FOR MEDICAL USE

DESCRIPTION

The present invention relates to a control handle for catheters or cannulas for medical use.

In particular, the present invention relates to a control handle used in surgical and clinical operations that envisage the insertion and movement of probes, catheters or cannulas in a determined anatomical part of the organism, for example, an artery of the human body. A particularly significant example is that of the handling of specific cannulas for the extraction of dielectric catheters implanted for permanent electrical cardiac stimulation with pacemakers or defibrillators.

Below, for simplicity purposes, the term tubular element will refer to elements that within the technical scope of the present invention require a control handle for their use, such as, for example, probes, catheters and cannulas.

Generally, tubular elements inserted in the patient's body to be handled with an external control handle are delicate medical devices intended for a treatment function and medical care that are just as delicate and require caution and skill also on the part of the specialist technical operator, usually a surgeon, in charge of using such instruments often with the use of their hands alone.

The most critical steps in the use of such elements are particularly the insertion and extraction due to the necessary flexibility of the tubular element.

In particular, its reduced cross section makes it difficult to grip and not easy to handle in the various stages of use.

Within the technical scope of the present invention, there is a control handle designed to handle the tubular element inserted in the different situations, providing the surgeon with control by gripping the aforementioned control handle directly with one hand.

The control handle in question performs various functions simultaneously, allowing greater control of the tubular element in the vein throughout the whole period of use and simultaneously preventing direct contact between the surgical gloves of the physician and the outer walls of the element itself, preventing possible causes of infection.

According to the current state of the art, there are various solutions available for handling tubular elements such as catheters or cannulas for medical use, but obviously almost all of them offer a gripping zone and a zone in which a determined effort or strain is engaged with one of such elements in order to drag, push or rotate it as preferred.

In a first solution [US2008262432 (A1)], for example, the control handle envisages an elongated body perforated from one side to the other across which the tubular element to be handled is inserted by passing it from one end to the other. On one of the two ends of the control handle from which the tubular element comes out, there is an elastic unit that surrounds a portion of the catheter along the whole format with at least three edges that are tightened onto the outer surface of the tubular element to be clamped by means of a ferrule assembled on the head of the control handle. The aforementioned ferrule can be unscrewed and/or screwed with the fingers while gripping the control handle in the palm of the hand.

In a different solution according to the prior art, [U.S. Pat. No. 6,533,772 (B1), U.S. Pat. No. 5,159,861 (A)] the control handle envisages a hollow body into which the tubular element is inserted at a free end to then be locked in position by a spring-loaded button or a "push to release" type elastic means, i.e. the element engaged by the spring-loaded button or the elastic means is free to slide within the body of the control handle only when the spring-loaded button or the elastic means are pressed with one finger of one hand, generally the hand gripping the entire device.

Usually in this solution, due to its own position, the element inserted into the control handle crosses a body solidly joined to the spring-loaded button or to the elastic means by means of a through hole: the activation of the button in the engagement position produces stress, prevalently shear stress, preventing all types of sliding of the locked element.

All the solutions of the prior art are subject to drawbacks and practical problems sometimes making the aforementioned control handle models for catheters or cannulas for medical use difficult to use in some specific situations or for particular technical reasons.

In general, all the solutions of the prior art envisage the insertion of the tubular element to be used by means of a through hole that forces the operator to have to insert it until the pre-established length necessary for performing the operation is reached, but which is generally variable during the procedure. Therefore, if it were necessary to move the element into a new specific position of its extension with respect to the control handle, it would have to be pulled out and/or pushed in every time through the control handle itself, which is generally always gripped by the surgeon concentrating on performing the operation. In fact, in order to be able to provide a sufficiently stable thrust, the control handle cannot be applied very far from the insertion point therefore repeated clamping-advancing-releasing-retracting steps are required in order to reach the desired position.

In reference to the solutions described and prevalent in the state of the art, the first solution that allows the element to be locked in position in order to make it controllable by means of a threaded ferrule does not allow the control handle of the catheter to be released quickly from the catheter until the control handle has slid along the entire extension of the catheter (which often has a significant length) when the control handle comes out of the distal end of the catheter itself, and the same thing happens for the insertion of the control handle on the catheter.

The second solution mentioned envisages in particular a "guillotine" locking method. In fact, the body of the spring-loaded button or other "push to release" type elastic means, is such as to strain the catheter prevalently in a couple of particular points (at the two inlet and outlet holes of the catheter from the body of the button) unloading only in these areas all the pressure generated by a button preloading spring or by a potential elastic element.

This concentrated mechanical strain can damage the handled element.

Furthermore, a "push to release" type system implies the constant action of at least one finger of the physician's hand whenever they wish to keep the catheter slidable and/or other items free to move inside, a situation that could tire the grip of the hand on the control handle and compromise the sensitivity of the hand itself in regulating the release step and the catheter locking step.

In this scope, the technical task of the present invention is providing a control handle which does not have the inconveniences cited above.

An object of the present invention is to provide a control handle that has high flexibility of use with respect to what is normally known within the specific technical field, i.e. whose coupling and decoupling with respect to the tubular element are immediate and easy to perform.

It is also an aim of the invention to provide a control handle that does not introduce any risk of damage to the tubular element inserted during the clamping and manoeuvring of the latter, thanks to quite a large contact surface between the element and the locking jaws.

These and other objects are substantially achieved by a control handle for tubular elements for medical use according to what is described in one or more of the appended claims.

Further characteristics and advantages will appear more clearly from the detailed description of a preferred, but not exclusive, embodiment of the control handle according to the present invention.

This description is provided with reference to the appended figures, also having a purely exemplificative and therefore non-limiting object, wherein the inserted element is a cannula for the extraction of electrical stimulators implanted in heart cavities.

FIG. 2 illustrates a sectional view of the control handle of FIG. 1A in accordance with a closure and clamping configuration of the control handle;

FIG. 3 illustrates a sectional view of the control handle of FIG. 1A in accordance with a closure and release configuration of the control handle;

FIG. 4A illustrates a control handle in accordance with a second embodiment of the invention in a cannula insertion configuration;

FIG. 4B illustrates a view of the control handle of FIG. 4A with the outer casing partially transparent in order to make the elements visible;

FIG. 5 illustrates a perspective view of the control handle with parts partially hidden in accordance with a third embodiment of the invention and in an insertion configuration of a cannula;

FIG. 6 illustrates a perspective view of the control handle in accordance with a third embodiment of the invention and in an insertion configuration of a cannula;

FIGS. 7A to 7C illustrate a sequence of steps for using the control handle of FIG. 1A according to the present invention.

Figure 1A:
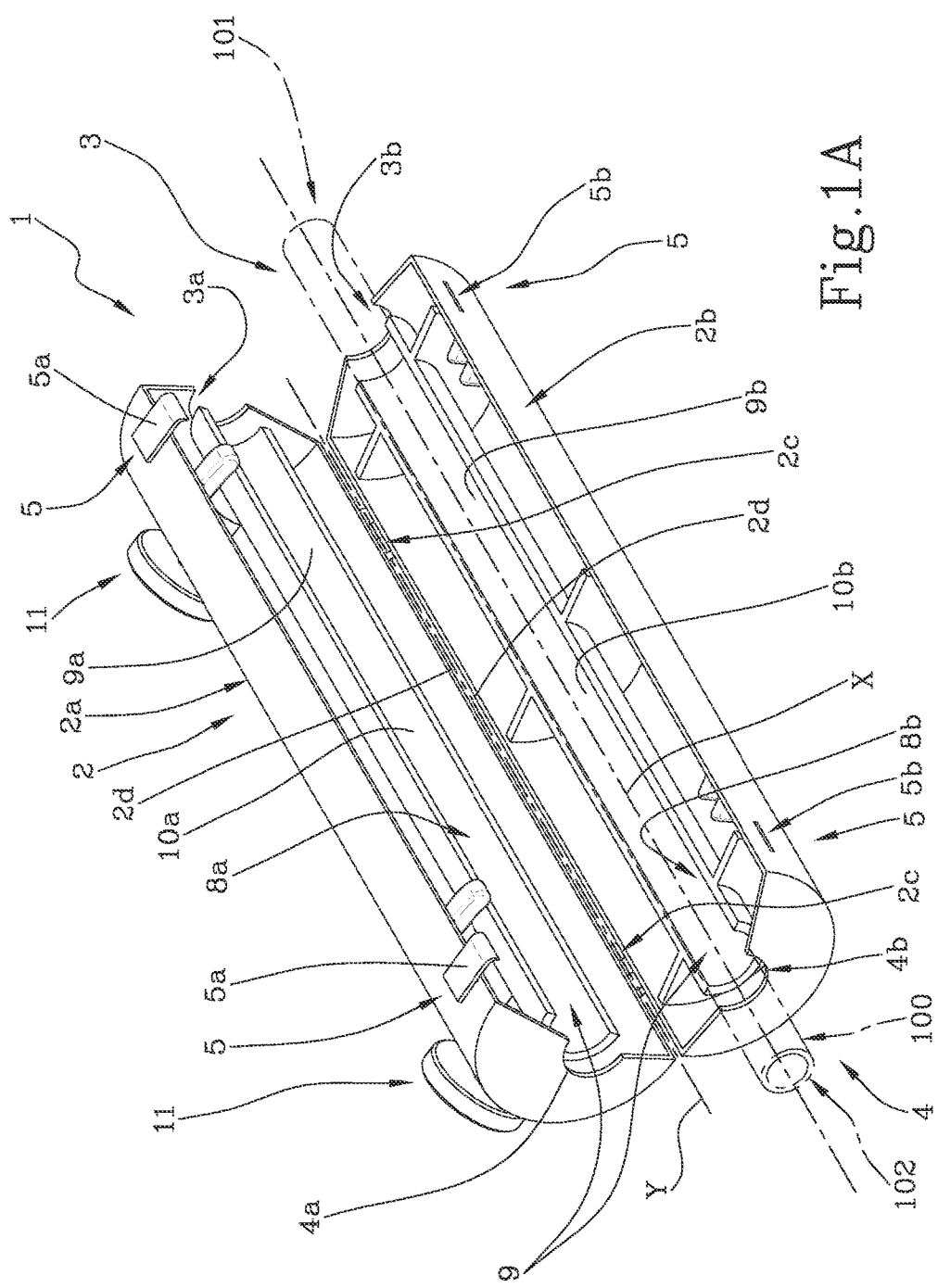
FIG. 1A illustrates a control handle in accordance with a first embodiment of the invention in a cannula insertion configuration.

In the appended figures a control handle has been illustrated as a whole with some embodiments included in the present invention but which are not exclusive.

The control handle in the appended figures is indicated overall by reference number 1.

In particular, the control handle 1 comprises an outer casing 2 having a first half-shell 2a and a second half shell 2b adapted to be moved away from each other for opening the control handle 1 and, alternatively, moved near each other for closing it.

Preferably, the half-shells 2a, 2b of the control handle 1 have such a shape that, in the closed half-shell 2a, 2b configuration, the closed outer casing 2 has a substantially cylindrical shape extending around a longitudinal axis "X" which preferably constitutes a prevalent axis of development of the control handle 1. Alternatively, the outer casing 2 could also be a different shape, as long as it is suitable for a stable grip by a user.

Preferably, the outer casing 2 further has a first longitudinal end 3 and a second longitudinal end 4 of the aforementioned cylinder, opposite one another along the aforementioned longitudinal axis "X".

Figure 1B:
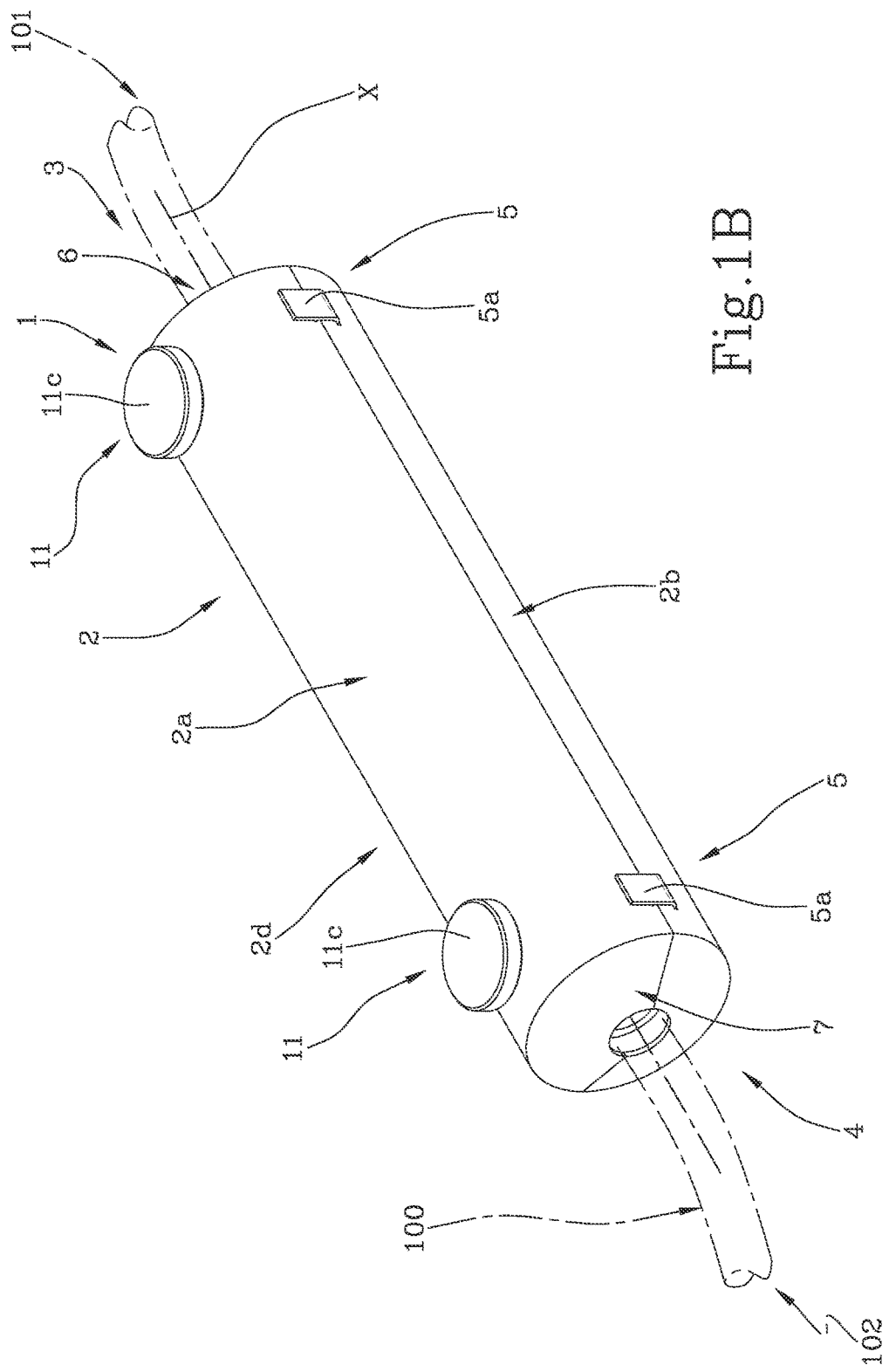
FIG. 1B illustrates the control handle of FIG. 1A in accordance with a clamping configuration of the control handle.

The casing 2 preferably has a connecting portion associated with a side portion of each half-shell 2a, 2b so as to define a flexible side connection 2c that allows relative movement between the two half-shells 2a, 2b (FIGS. 1A, 1B).

In detail, the flexible side connection 2c between the two half-shells 2a, 2b preferably comprises a hinge or a flexible rotation system defining an axis of rotation "Y" along a longitudinal edge 2d of the half-shells 2a, 2b such as the example illustrated in the appended FIG. 1A.

The longitudinal axis "X" and the axis of rotation "Y" can be parallel to one another or inclined with respect to one another.

In other words, the longitudinal axis of development "X" of the casing 2 is parallel to the axis of rotation (hinge) "Y" of the two half-shells 2a, 2b when the casing 2 is cylindrical, such as in the configuration illustrated in the appended FIGS. 2 and 3 where the control handle 1 is shown in a closure and clamping configuration and a closure and release configuration, respectively.

Preferably, in the embodiment that envisages the cylindrical casing 2, the diameter is comprised between a value of 30 mm and a value of 45 mm.

By way of example, in a different configuration of the invention, the casing 2 has a conical or troncoconical shape so that the longitudinal axis "X" of the casing 2 is incident with respect to the axis of rotation "Y" of the half-shells 2a, 2b. This shape of the invention is not shown in the appended figures.

In a different embodiment of the invention, such as that illustrated in FIG. 5, the connection between the two half-shells 2a, 2b preferably comprises a hinge or a flexible rotation system defining an axis of rotation "T" arranged transversally with respect to the longitudinal axis of development "X"; preferably the axis "T" is arranged perpendicular to the longitudinal axis "X".

In other words, the axis of rotation "T" of the hinge or flexible system and that allows the relative opening and closing movement between the two half-shells 2a, 2b is arranged along one of the shorter sides of the cylindrical casing 2, preferably at the second longitudinal end 4 of the device 1, i.e. the rear one of the control handle 1.

Preferably, the hinge 2c can be integrated with the two half-shells 2a, 2b, for example made by means of moulding in a single operation, or the hinge 2c may be separate from the half-shells 2a, 2b and assembled during the assembly of the control handle 1.

Furthermore, the hinge 2c can be defined by a continuous joining edge of the two half-shells 2a, 2b (which extends along the entire longitudinal development of the two half-shells 2a, 2b along the axis of rotation "Y" or along the axis of rotation "T") or, alternatively, by a plurality of discrete connecting elements rotatable and flexible between the two half-shells 2a, 2b.

In a further and different embodiment of the invention, not illustrated in the appended figures, preferably the half-shells 2a, 2b are separate and distinct, therefore they do not have any permanent joining elements, either continuously or discretely, along an edge of the half-shells 2a, 2b themselves.

Preferably, the control handle 1 comprises closing means 5 acting between the two half-shells 2a, 2b to keep the two half-shells stable in the configuration in which they are moved near each other. Preferably, said closing means 5 are of the snap type. In a possible embodiment, the closing means 5 comprise at least one hooked portion 5a fixed onto the first half-shell 2a while the second half-shell 2b has at least one corresponding slot 5b adapted for engagement with the aforementioned hooked portion 5a. In the embodiment illustrated in FIGS. 1A-3, the closing means 5 comprise two hooked portions 5a and two corresponding slots 5b defining two reciprocal anchoring points between the half-shells 2a, 2b. Such anchoring points are arranged in two external points of the outer casing 2 (in proximity to the longitudinal ends 3 and 4) and in the distal position with respect to the longitudinal edge 2d.

In reference to what is shown in the appended FIG. 5, the device 1 has closing means 5 configured so as to also make the hinge or the connection during a configuration of moving the two half-shells 2a, 2b near or away from each other. In particular, at a second longitudinal end 4 a hooked portion 5a acts as a hinge between the first half-shell 2a and the second half-shell 2b, while at the first longitudinal end 3 a hooked portion 5a constrained onto the second half-shell 2b acts as a snap closure interacting in a slot 5b arranged on the half-shell 2a, Preferably, the two half-shells 2a, 2b are completely detachable from one another allowing the transversal insertion of a portion of the cannula 100.

In reference to what is illustrated in FIG. 6, the closing means 5 comprise at least one guide 5c that extends partially along an outer perimetric line for example of the second half-shell 2b and at least one locking element 5d arranged for example at the first half-shell 2a. Preferably, the locking element 5d is adapted to be coupled slidably with the aforementioned guide 5c through a rotation about the axis "X". Furthermore, both the guides 5c and the sliding element 5d are arranged on a perpendicular plane to the mentioned longitudinal axis "X". Therefore, a rotation of at least one locking element 5d about the longitudinal axis "X" allows the activation of the closing means 5, with the locking element 5d inserted in the guide 5c. The casing 2 in this condition is reversibly closed. The rotation of the locking element 5d in the opposite direction implies the deactivation of the closing means 5 once the locking element 5d is disengaged from the guide 5c. In this condition the casing 2 can be opened.

In a different embodiment not illustrated in the appended figures, the closing means 5 comprise a body having a portion with a slider shape, adapted to interact with a portion of a finger of a user, for example, with a knurled surface, and an opposite portion to the slider shaped portion having a tooth or a relief adapted to interact with a slot or a stopping edge for performing the closure between the two half-shells 2a, 2b.

The closing means 5 can also comprise other embodiments, not illustrated, in accordance with the inventive concept of the invention and which are arranged for continuous activation/deactivation during the use of the control handle 1.

In particular, the closing means 5 can be integrated into a single structure of the casing 2, or integral with the casing 2, allowing simple and quick use by a user, particularly during the activation/deactivation operation of the closing means 5 themselves.

Each half-shell 2a, 2b has, at the respective longitudinal ends 3, 4 semi-circular breaks 3a, 4a; 3b, 4b which, in mutual cooperation with the semi-circular breaks 3a, 4a; 3b, 4b of the other half-shells 2a, 2b in the closed configuration of the half-shells 2a, 2b, define respective longitudinally opposite openings adapted for the passage of the cannula 100. The cannula 100 is therefore trapped in the control handle 1 when the casing 2 is in the closure configuration (movement of the half-shells 2a, 2b near to each other) while it can be applied or removed onto/from the control handle 1 in the opening configuration (movement of the half-shells 2a, 2b away from each other).

Each half-shell 2a, 2b defines an internal volume 8a and 8b facing the other half-shell 2b, 2a and within which gripping means are housed for firmly gripping a cannula 100 in a configuration of the control handle 1 applied to the cannula 100.

In a preferred embodiment, and in accordance with the appended figures, the gripping means comprise a pair of jaws 9a, 9b each associated with a respective half-shell 2a, 2b and in particular inserted into the respective internal volume 8a, 8b.

Preferably, the jaws 9a, 9b cooperate with each other to define a clamping member 9 adapted to assume a closed configuration in which it delimits, within itself, a housing seat 10 for a portion of the cannula 100. In detail, the housing seat 10 defines an inner surface having a section adapted to interact with the portion of cannula 100 contained therein.

In an alternative embodiment, not illustrated in the appended figures, at least one jaw 9a, 9b has a flat cross section. Preferably, the casing 2 in the case of at least one receiving portion 10a, 10b having a flat shape, has a larger outer diameter than indicated above, even more preferably an outer diameter that is about 1 cm longer than the aforementioned measurements.

In a further and different embodiment as illustrated in FIG. 4B, at least one jaw 9a, 9b has a cross section defined by an open broken line that provides a housing bed for the cannula 100.

In any case, the receiving surface 10a, 10b has a suitable shape for partially surrounding a portion of the cannula 100 with different outer diameter measurements.

Preferably, the first jaw 9a has a shaping with a curved shaped section while the second jaw 9b, opposite the first 9a, has a semi-circular section defining the receiving surface 10b, 10a of the housing seat 10 according to a pre-arranged measurement of the radius of such semi-circular section.

The two jaws can be equipped with different shapings according to the specific use of the control handle.

Preferably, the housing seat 10 is arranged in a parallel direction to the longitudinal axis "X", so that the transversal insertion and/or de-insertion of the portion of cannula 100 is easier when the half-shells 2a, 2b of the casing 2 are in the configuration of moving away from each other.

This geometric solution of parallelism between the housing seat 10 and the longitudinal axis "X" is in accordance with the preferred embodiment of the invention, but further geometric solutions other than the preferred one are however covered by the present invention. The variations mentioned here are not illustrated in the appended figures.

Preferably, the jaws 9a, 9b are made of plastic material suitable for medical use and to be used in surgical operations, also having suitable mechanical rigidity characteristics.

In particular, the jaws 9a, 9b have at the respective receiving surfaces 10a, 10b a layer of deformable elastic material with a high coefficient of friction applied onto the plastic material of which the jaw is made.

This layer of deformable elastic material is such as to generate friction with the material of the cannula 100 so as to prevent its involuntary sliding and at the same time allow a torsion force to be applied.

Preferably, the layer of deformable material present on the jaws 9a, 9b may be, by way of example, a silicone resin or a rubbery material of another kind.

The deformable material may be, by way of example, co-moulded along with the body of the jaw or may be in the form of strips applied to the jaws 9a, 9b during assembly.

In a different embodiment of the jaws 9a, 9b not illustrated in the appended figures, the body of at least one jaw 9a, 9b is made entirely of flexible silicone material with a high coefficient of friction.

Preferably, the jaws 9a, 9b extend longitudinally along a parallel direction to the axis of development "X" of the casing 2 between the first longitudinal end 3 and the second longitudinal end 4.

In the configuration of the half-shells 2a, 2b being moved away from each other or when there is no compression by the jaws 9a, 9b on the portion of the cannula 100, the latter simply slips onto the second jaw 9b, preferably the one arranged below the other, with modest friction between the respective surfaces.

In the aforementioned configuration of the half-shells 2a, 2b being moved near each other, the clamping member 9 can assume a configuration in which the jaws 9a, 9b cooperate with each other tightening around the aforementioned portion of the cannula 100 housed in the aforementioned seat 10.

In particular, the jaws 9a, 9b preferably with the aforementioned layer of deformable material fully clamped, are such that the two receiving surfaces 10a, 10b move towards each other and are substantially deformed so as to allow effective contact with the outer surface of the portion of cannula 100 contained within them.

In accordance with the present invention, the jaws 9a, 9b have a different longitudinal extension, preferably according to two different measurement intervals. In other words, the jaws 9a, 9b may have two different pre-established lengths.

Based on the extension measurement the jaws can be split into at least two categories, called, by way of example, "short jaws" in a first category and "long jaws" in a second category.

The so-called "short" jaws 9a, 9b have a longitudinal extension by way of example between 2 and 4 cm.

The so-called "long" jaws 9a, 9b have a longitudinal extension by way of example comprised between 5 and 7 cm.

Preferably, the so-called "short" jaws 9a, 9b are arranged in proximity to the first longitudinal end 3 of the device 1, or the front one, that is, facing the inlet point into the patient. In particular, the so-called "short" jaws 9a, 9b are preferably indicated to interact with a rather flexible cannula 100.

In fact, the modest longitudinal extension of the jaws 9a, 9b that distinguishes the "short" jaws implies respective receiving surfaces 10a, 10b with a reduced extension and therefore a reduced friction surface.

In a configuration of the half-shells 2a, 2b being moved away from each other, the modest friction created with the portion of the cannula 100 still arranged between the jaws 9a, 9b, in particular on the second jaw 9b allows easy sliding of the cannula 100 on it.

Preferably the so-called "long" jaws 9a, 9b are arranged in the portion of the device 1 comprised between the first longitudinal end 3 and the second longitudinal end 4. In other words, the "long" jaws 9a, 9b are preferably arranged in a central area of the outer casing 2 of the device 1 with respect to the axis of development "X".

In accordance with the embodiments comprised herein, the control handle 1 has at least on the first of the two half-shells 2a, 2b, driving means 11 acting on the respective jaw 9a for moving the jaw 9a away from and towards the other jaw 9b so as to clamp and release the mentioned clamping member 9.

In other words, according to the invention a first jaw 9a is mobile under the action of the driving means 11 while the second jaw 9b is removably housed within the internal volume 8b of the respective half-shell 2b, for example, with an interlocking system that can be unlocked manually or with other systems suitable for that purpose. For example, the second jaw 9b can be made integral with the respective half-shell 2b, hence defining an inner portion of the second half-shell 2b itself.

In one embodiment of the driving means 11 they are of the screw type, with at least one threaded element applied directly onto one jaw 9a, 9b, as illustrated in the appended FIGS. 1A-3.

In particular the screw type driving means 11 comprise two threaded members 11a each having a shaft 11b screwed into a threaded hole 2e fashioned on the respective half-shell, the shaft 11b projecting outside the half-shell 2a. The two threaded members 11a each have a rotatable knob 11c solidly joined to the shaft 11b and arranged outside the half-shell 2a so as to allow a rotation manoeuvre of the threaded members 11a, 11b.

Furthermore, the two threaded members 11a have on the opposite side to each rotatable knob 11c an end 11d connected in a freely rotatable way, for example, with an engagement with a retaining edge, in a respective receiving portion "P" of the jaw 9a.

For greater precision, the term rotatable knob 11c covers different shapes and solutions for driving a threaded member 11a, for example, it comprises a cylindrical control handle or one shaped for a better grip with the fingers of one hand, or it could be of the "butterfly" type or a rotatable lever.

Therefore, by acting on the driving means 11 a release configuration of the clamping member 9 by unscrewing both the rotatable knobs 11c and a clamping configuration of the clamping member 9 by screwing both rotatable knobs 11c, are performed respectively.

The two threaded members 11a, 11b are arranged in alignment along a parallel direction to the longitudinal axis "X" of the casing 2 so as to be able to allow a uniform thrust on the first jaw 9a, for example, at the ends of the latter.

Further embodiments of the invention other than the preferred one and covered by the present invention, envisage the driving means 11 comprising a different number of threaded elements, for example only one or two or more (in this case preferably arranged in alignment along a parallel direction to the longitudinal axis "X" of the casing 2). By way of example, the number of threaded members can be chosen according to the longitudinal length of the jaws 9a, 9b, or according to the "short" category of jaws or the "long" category so as to guarantee a clamping action distributed uniformly along the entire longitudinal extension of the jaws 9a, 9b themselves.

In a further and different embodiment of the invention not illustrated in the appended figures, both jaws 9a, 9b are mobile and adjustable with the driving means 11 applied to both half-shells 2a and 2b, therefore with female screw-screw type elements or with screw type elements simultaneously active on the half-shells 2a and 2b of the outer casing 2.

In particular, in a different embodiment illustrated in FIGS. 4A-6 the driving means 11 active on one jaw 9a, 9b for moving it away from and towards the other jaw 9a, 9b are of the female screw-screw type, i.e. they comprise at least one coupling between a female screw element 12 and a screw element 13.

In other words, said female screw element 12 is rotatably constrained in the respective inner part 8a, 8b of a half-shell 2a, 2b of the device 1 and has, by way of example, the shape of a circular slider with a threaded through hole 12a at its axis of rotation "Z".

For convenience and descriptive ease the female screw element 12 shall be referred to hereinafter as a circular slider 12.

Preferably, the circular slider 12 lies on a parallel plane to the closing plane of the jaws 9a, 9b of the control handle 1, even more preferably the axis of rotation "Z" of the slider 12 is perpendicular to and intersects the longitudinal axis of development "X" of the casing 2.

The circular slider 12 has a diameter such that the circular profile 12b projects laterally in one or more opposite points of at least one of the half-shells 2a, 2b. Appropriate openings 14a, 14b or slots afforded on the half shell 2a, 2b at the projections of the slider 12 ensure that the circular slider 12 is visible and accessible with the fingers of one hand from the outside of the half-shell 2a, 2b when the device 1 is gripped. Furthermore, the circular slider 12 can have a circular profile 12b with a tapered shape, by way of example troncoconical, so as to follow the line of curvature of the cross section of the casing 2 at the axis of rotation "Z" of the slider 12.

In order to facilitate the grip on the slider 12 by a user, the circular slider 12 preferably has a surface to facilitate the manoeuvre along the circular profile 12b. In another embodiment, the circular slider 12, not illustrated in the appended figures, can preferably have levers, one for each opening 14a, 14b projecting from the openings 14a, 14b themselves and adapted to be activated with a movement along the whole longitudinal extension of the opening 14a, 14b which, for example, can correspond to a rotation of the slider 12 equal to a quarter of a turn about the axis "Z". Preferably, such a rotation is sufficient to reach the maximum compression position of the jaws 9a, 9b on the portion of the cannula 100 housed between them.

In particular, according to the type of jaw used in the specific embodiment of the device 1, return springs 11e can be inserted along the extension of the casing 2 that promote the opening of the jaws 9a, 9b, as can be seen in FIGS. 4B and 5.

In other words, the insertion of the return springs 11e between a half-shell 2a, 2b and the respective jaw 9a, 9b allows, when the driving means 11 are not activated, a situation to arise wherein the jaws 9a, 9b are returned to a non-compression situation on the outer surface of the cannula 100.

The screw element 13 coupled with the circular slider 12 extends along two ends 13a, 13b aligned with the axis of rotation "Z". The first end 13a is threaded so as to be screwed into the threaded hole 12a of the circular slider 12, while the second end 13b is fixed or constrained to a jaw 9a, 9b at the opposite side to the respective receiving surface 10a, 10b.

By way of example, a rotation in one direction of the circular slider 12 implies the screwing of the screw element 13 into the threaded hole 12a and therefore the simultaneous movement of a jaw 9a away from the opposite jaw 9b. Vice versa, a rotation in the opposite direction of the slider 12 implies the unscrewing of the element 13 from the threaded hole 12a and therefore a simultaneous movement of one jaw 9a towards the opposite jaw 9b causing the clamping of the cannula 100.

Preferably, the diameter of the circular profile 12b of the circular slider 12 is comprised between a value of 30 mm and a value of 50 mm, even more preferably comprised between a value of 40 mm and a value of 45 mm.

In a further and different embodiment of the driving means 11, not illustrated in the appended figures, they comprise the circular slider 12 completely built into one of the half-shells 2a, 2b. The circular slider 12 meshes with one of the teeth on the circular profile 12b with a worm screw type slider which is rotatably constrained to a half-shell 2a, 2b and partially protrudes externally to a half-shell 2a, 2b. The worm screw slider is rotatable about an axis preferably parallel to the longitudinal axis "X" and is structured so as to be able to be activated with the fingers of one hand.

In a further and different embodiment of the driving means 11, not illustrated in the appended figures, the screw element is no longer driven by a control handle 11c external to a half-shell 2a, 2b but by means of a built-in seat with a shape such as to permit the insertion of a shaped key or the head of a screwdriver.

In reference to the embodiments comprised within the concept of the present invention, the screw driving means 11 preferably comprise locking means on at least one of the two rotatable knobs 11c, even more preferably they have a locking ring on the rotatable knob 11c associated with the first half-shell 2a.

The combination of a specific length of the jaws 9a, 9b of the "short" or "long" type with a particular embodiment of the driving means 11, allows different embodiments to be obtained all covered by the present invention and only illustrated in part in the appended figures. In particular, the rule can be assumed that for jaws 9a, 9b of the "short" category, the number of driving means 11 is preferably reduced to a single element of driving means 11.

In the event that the device 1 has jaws 9a, 9b in the "long" category, the driving means 11 will preferably be uniformly distributed along the longitudinal extension of the jaws 9a, 9b themselves with various elements active between the half-shell 2a, 2b and the respective jaw 9a, 9b, for example at least two active elements of said driving means 11.

In a configuration of use of the control handle 1, the outer casing 2 in the closed configuration has the cannula 100 inserted reversibly contained within the housing seat 10 for one portion of it (clampable and releasable through the respective activation of the driving means 11) and coming out of the control handle 1 from the first longitudinal opening 6 towards a first end of it 101 and from the second longitudinal opening 7 towards a second distal end 102 to the first end 101.

Preferably, to facilitate the sliding along the cannula 100 of the control handle 1, two closure configurations of the half-shells 2a, 2b can be performed, conventionally defined as total closure and partial closure.

In accordance with a total closure configuration the two half-shells 2a, 2b are arranged reciprocally near to each other and the closing means 5 are activated. The driving means 11 are also activated so as to clamp the jaws 9a, 9b and bring the receiving surfaces 10a, 10b to retain by friction a portion of the cannula 100. In this total closure configuration, the control handle 1 cannot slide along the cannula 100, not even by voluntarily forcing it.

In accordance with a partial closure configuration the half-shells 2a, 2b are placed away from each other, therefore there is no opposition of friction, at least partially, to the sliding of the control handle 1 along the cannula 100.

In other words, starting from the activation of the driving means 11 the equal and unvaried in the position with respect to the activation used in the total closure configuration, the open position of the half-shells 2a, 2b deactivates the grip by friction of the receiving surfaces 10a, 10b on a portion of the cannula 100 allowing the control handle 1 to slide freely.

After the user has performed a pre-established sliding of the control handle 1, it can be brought back into the total closure configuration placing the half-shells 2a, 2b near to each other and activating the closing means 5. In this way the compression force of the receiving portions 10a, 10b of the jaws 9a, 9b is restored without having to act on the driving means 1 being, for example, already pre-set previously during a first stage of use of the control handle 1. In the appended FIGS. 7A-7C, a sequence of steps is illustrated envisaging the insertion and extraction of a cannula 100, through a through hole using a control handle 1, as per FIGS. 1A-3. In all the steps illustrated in the aforementioned sequence, the control handle 1 is shown in the closed configuration around the cannula 100, therefore ready for movement since the steps of application and extraction of the cannula 100 onto/from the control handle 1 are clearly deducible from the above description.

In particular, the appended FIG. 7a illustrates a preliminary insertion of the cannula 100 into a vessel of a patient by means of the control handle 1 according to the invention. In this situation, the control handle 1 is already applied to the cannula 100 and clamped onto it at a distance, with respect to the vessel, such as to allow the correct thrust action on the cannula 100.

Subsequently, the user grips the control handle 1 and, taking hold of it, pushes the cannula 100 deep into the vessel up to a position in which the control handle 1 is in proximity to the inlet point into the vessel. In such a condition (FIG. 7B) it is necessary to withdraw the control handle 1 with respect to the cannula 100 to allow a subsequent advancement action of a subsequent section of the cannula 100 in the patient's vessel.

Preferably, starting from the position in FIG. 7B, the user of the control handle 1 has at least two options for use.

In a first option the user of the control handle 1 unscrews the rotatable knobs 11c of the driving means 11 of the control handle 1 to release the clamping member 9 and pull out the control handle 1 along the cannula 100 and bring it into a more retracted position, suitable to exert a subsequent correct thrust action thereon (FIG. 7C). Having reached that position, the user acts again on the rotatable knobs 11c of the driving means 11 bringing the clamping member 9 into the clamping position and therefore producing the additional advancement of the cannula 100 in the vessel.

This sequence of operations can be repeated until the desired level of insertion of the cannula 100 in the vessel is obtained.

Having concluded the user condition, the cannula 100 can be extracted from the through hole transversally to it by opening the casing 2 rotating the two half-shells 2a, 2b between each other, hence opening the housing seat 10.

In a second option the user places the control handle 1 in the partial closure configuration, i.e. with the two half-shells 2a, 2b open and without intervening on the driving means 11 but only acting on the closing means 5. In this way the control handle 1 is open and free to be repositioned along the cannula 100 and then subsequently be brought back into the total closure configuration still acting only on the closing means 5.

Advantageously, the procedure illustrated in the second option allows the quick and effective control action of a user on the control handle 1 acting only on the closing means 5 and omitting the adjustment of the clamping member 9 which can only be set once for the type of cannula 100 being used, for example, when it is inserted for the first time in the control handle 1.

The control handle 1, according to the present invention, allows it to be closed around a portion of the cannula 100 quickly and without the control handle 1 being made to slide all the way along the extension of the cannula 100 until the control handle comes out of a distal end of the cannula 100 itself. This is enabled by fashioning the casing in two half-shells hinged to one another which, in the configuration in which they are completely away from each other, allow the removal of the cannula in the transversal direction.

Advantageously, the housing seat 10 of the portion of cannula 100 inserted in the control handle 1 envisages a large extension of the receiving surfaces 10a, 10b and this allows the surface pressure on the walls of the cannula facing the aforementioned surfaces 10a, 10b to be notably reduced when they are clamped. The reduced mechanical pressure makes the control handle 1 suitable for all models of cannula, even for more delicate catheters.

Advantageously, the driving means 11 comprise threaded elements that can be activated through a rotatable knob 11c or a circular slider 12, eliminating known snap or button systems that imply the constant action of at least one finger of the hand of the user whenever the cannula needs to be kept slidable and/or other objects free to move within it or the unnatural position of some fingers of the hand for always acting on the aforementioned closure/release systems.

Furthermore, advantageously, the driving means 11 described allow the fine adjustment of the mechanical pressure exerted on the receiving surfaces 10a, 10b on the portion of cannula 100 directly by the user of the control handle 1 without any particular effort by the operator.

Advantageously, the deposition of a layer of deformable material on the receiving surface 10a, 10b of each jaw 9a, 9b allows the perfect closure on the portion of cannula 100 housed in the device 1, adapting the shape of the jaws 9a, 9b to the external measurement of the portion of cannula 100 itself and the external geometry thereof.

Advantageously, the layer of deformable material also has a high coefficient of friction. High friction between the receiving surfaces 10a, 10b and the outer surface of the portion of cannula 100 allows optimal control thereof in all conditions of use and furthermore allows accidental involuntary sliding of the control handle 1 to be avoided. Furthermore, a high coefficient of friction of the jaws 9a, 9b allows an excellent grip to be ensured also with a lower longitudinal extension of the actual jaws with respect to the prior art, optimising the dimensions and overall size of the control handle 1, especially in terms of the longitudinal extension along the axis "X".

Advantageously, the snap closing means 5 for closing the half-shells makes it quicker and simpler to switch from a configuration in which the half-shells 2a, 2b are away from each other for opening the control handle 1 and one in which they are near each other for closing it. Furthermore, the presence of a flexible side connection 2c, in particular by means of a hinge, allows the half-shells 2a, 2b of the casing 2 to be united facilitating the grip and the closure of the casing 2 with a single hand of the user leaving the other hand free.

Advantageously, the possibility of a double closure configuration of the control handle 1, i.e. a total closure configuration or a partial closure configuration, allows each embodiment of the control handle 1 to be used easily and safely, in particular the embodiment of the control handle 1 with the "long" jaws and with the "short" jaws.

Even more advantageously, the double closure configuration (total or partial) allows the user to have excellent control and grip, even in the event of a torsion movement of the cannula, during the use of a control handle 1 equipped with "long" jaws, at the same time preventing accidental engagement by friction during the sliding operation.

Advantageously, in a configuration of the control handle 1 wherein the flexible side connection 2c has a perpendicular axis of rotation "T" to the longitudinal axis "X" of the casing 2, the closing means 5 absolve their specific function and at the same time allow the opening/closing of the half-shells 2a, 2b to be accompanied as if they were real hinges, on at least one of the hooked portions 5a.

The half-shell solution 2a, 2b of the control handle 1 allows the storage of sterile packaging of the control handle 1 itself to be optimised which, once assembled, does not have separate parts and/or to be assembled once the package is open immediately before using the control handle 1 itself.

Advantageously, the presence of separate and adaptable jaws 9a, 9b allows a single casing 2 to be used and a variety of different cannula 100 measurements, offering greater possibility of use of the control handle 1.

Advantageously, the control handle 1 allows the clamping force between the aforementioned receiving portions 10a, 10b and a portion of the outer wall of a cannula 100 to be activated/deactivated whenever the control handle 1 is used and/or every time a user needs it.

Advantageously, the control handle 1 according to the present invention allows the calibration of the clamping force between a housing seat 10 of the control handle 1 and a portion of the cannula 100 regardless of the measurement of its diameter.

Preferably, the longitudinal cylindrical extension of the casing 2 and the measurement of its outer diameter is such as to offer an effective gripping surface for the user's hand.

The invention claimed is:

1. A control handle (1) for a tubular element (100) for medical use, comprising:
   an outer casing (2) comprising a first half-shell (2a) and a second half-shell (2b) configurable in at least a configuration of being moved away from each other adapted to enable the insertion of at least a portion of the tubular element (100) between the two half-shells (2a, 2b), and a configuration of being moved near each other adapted to close over said portion of the tubular element (100), wherein each half-shell (2a, 2b) has a respective jaw (9a, 9b), the jaws (9a, 9b) of the two half-shells (2a, 2b) cooperating with each other to define a clamping member (9) suitable for being tightened around said portion of the tubular element (100);
   driving means (11), applied on at least one of said half-shells (2a, 2b) and acting upon the respective jaw (9a, 9b) to move said jaw (9a, 9b) away from and toward the other jaw (9b, 9a) so as to produce, respectively, a release configuration and a clamping configuration of said clamping member (9);
characterized in that it further comprises closing means (5) acting between the two half-shells (2a, 2b) so as to maintain the two half-shells (2a, 2b) stably in said configuration of being near each other, said closing means (5) comprising snap means (5a, 5b) such as to enable said control handle (1) to assume, alternatively, at least one configuration of total closure or a configuration of partial closure;
wherein said snap means comprise at least one hooked portion (5a) fixed onto the first half-shell (2a) while the second half-shell (2b) has at least one corresponding slot (5b) adapted for engagement with said hooked portion (5a).

2. The control handle (1) according to claim 1, wherein the jaws (9a, 9b) comprise, at least on their respective receiving surfaces (10a, 10b), a layer of deformable elastic material with a high coefficient of friction.

3. The control handle (1) according to claim 1, wherein at least one jaw (9a, 9b) has a cross section defined by an open broken line having at least three adjacent segments and defining a receiving surface (10a) for the portion of the tubular element (100).

4. The control handle (1) according to claim 1, wherein each jaw (9a, 9b) extends in a main longitudinal direction comprised between 1 and 7 cm.

5. The control handle (1) according to claim 1, wherein said driving means (11) are applied only on one of said half-shells (2a, 2b) and wherein the jaw (9a, 9b) of the other half-shell (2b, 2a) is stably fixed to the other half-shell (2b, 2a).

6. The control handle (1) according to claim 1, wherein said half-shells (2a, 2b) are connected to each other by means of a hinge-type side connection (2c) defining a rotation axis ("Y") along a longitudinal edge (2d) of said half-shells (2a, 2b).

7. The control handle (1) according to claim 1, wherein said half-shells (2a, 2b) are connected to each other by means of a hinge-type connection (2c) defining a rotation axis ("T") along an edge that is transverse to said longitudinal edge (2d) of said half-shells (2a, 2b), said rotation axis ("T") being perpendicular to said longitudinal axis ("X") along which the casing (2) extends.

8. The control handle (1) according to claim 1, wherein said first half-shell (2a) and said second half-shell (2b) are connected to each other in a respective side connecting portion defining a flexible side connection (2c).

9. The control handle (1) according to claim 1, wherein said driving means (11) comprise a female screw element (12) coupled to a screw member (13), said screw member (13) being fixed onto the respective jaw (9a, 9b) of the respective half-shell (2a, 2b) so as to move said respective jaw (9a, 9b) away from and toward the opposite jaw (9b,9a).

10. The control handle (1) according to claim 9, wherein said female screw element (12) is rotatably constrained to the respective half-shell (2a, 2b) and at least partially enclosed in the inner part (8a, 8b) of said respective half-shell (2a, 2b) and protrudes externally relative to said respective half-shell (2a, 2b) through at least two openings (14a, 14b) disposed symmetrically on opposite sides of the outer surface of the respective half-shell (2a, 2b).

11. The control handle (1) according to claim 9, wherein said screw driving means (11) comprise at least one threaded member (11a) screwed into a respective threaded hole (2e) fashioned in said first half-shell (2a) and coupled to the jaw (9a) of said first half-shell (2a) so as to move said jaw (9a) away from and toward the other jaw (9b), and wherein said driving means (11) comprise at least two threaded members (11a) screwed into respective threaded holes (2e) fashioned in said first half-shell (2a) and acting upon two different portions of said jaw (9a) of the first half-shell (2a).

12. The control handle (1) according to claim 1, wherein said driving means (11) are of the screw type.

13. The control handle (1) according to claim 12, wherein said screw driving means (11) comprise at least one threaded member (11a) screwed into a respective threaded hole (2e) fashioned in said first half-shell (2a) and coupled to the jaw (9a) of said first half-shell (2a) so as to move said jaw (9a) away from and toward the other jaw (9b).

14. The control handle (1) according to claim 13, wherein said threaded member (11a) comprises a shaft (11b), screwed into said threaded hole (2e) and projecting outside said first half-shell (2a), and a rotatable knob (11c) solidly joined to said shaft (11b) and disposed outside said first half-shell (2a).

15. The control handle (1) according to claim 14, wherein said threaded member (11a) has an end (11d) opposite said rotatable knob (11c), connected in a freely rotatable manner to a respective receiving portion (P) of said jaw (9a) of the first half-shell (2a).

16. A control handle (1) for a tubular element (100) for medical use, comprising:
an outer casing (2) comprising a first half-shell (2a) and a second half-shell (2b) configurable in at least a configuration of being moved away from each other adapted to enable the insertion of at least a portion of the tubular element (100) between the two half-shells (2a, 2b), and a configuration of being moved near each other adapted to close over said portion of the tubular element (100), wherein each half-shell (2a, 2b) has a respective jaw (9a, 9b), the jaws (9a, 9b) of the two half-shells (2a, 2b) cooperating with each other to define a clamping member (9) suitable for being tightened around said portion of the tubular element (100);
driving means (11), applied on at least one of said half-shells (2a, 2b) and acting upon the respective jaw (9a, 9b) to move said jaw (9a, 9b) away from and toward the other jaw (9b, 9a) so as to produce, respectively, a release configuration and a clamping configuration of said clamping member (9);
characterized in that it further comprises closing means (5) acting between the two half-shells (2a, 2b) so as to maintain the two half-shells (2a, 2b) stably in said configuration of being near each other, said closing means (5) comprising snap means (5a, 5b) such as to enable said control handle (1) to assume, alternatively, at least one configuration of total closure or a configuration of partial closure;
wherein said closing means comprise at least one guide (5c) that extends partially along an outer perimetric line of the second half-shell (2b) and at least one locking element (5d) arranged at the first half-shell (2a), said locking element (5d) being adapted to be coupled slidably with said guide (5c) through a rotation about the axis "X".

17. The control handle (1) according to claim 16, wherein said driving means (11) are of the screw type.

18. The control handle (1) according to claim 16, wherein the jaws (9a, 9b) comprise, at least on their respective receiving surfaces (10a, 10b), a layer of deformable elastic material with a high coefficient of friction.

19. The control handle (1) according to claim 16, wherein at least one jaw (9a, 9b) has a cross section defined by an open broken line having at least three adjacent segments and defining a receiving surface (10a) for the portion of the tubular element (100).

20. The control handle (1) according to claim 16, wherein each jaw (9a, 9b) extends in a main longitudinal direction comprised between 1 and 7 cm.

21. The control handle (1) according to claim 16, wherein said driving means (11) are applied only on one of said half-shells (2a, 2b) and wherein the jaw (9a, 9b) of the other half-shell (2b, 2a) is stably fixed to the other half-shell (2b, 2a).

22. The control handle (1) according to claim 16, wherein said half-shells (2a, 2b) are connected to each other by means of a hinge-type side connection (2c) defining a rotation axis ("Y") along a longitudinal edge (2d) of said half-shells (2a, 2b).

23. The control handle (1) according to claim 16, wherein said half-shells (2a, 2b) are connected to each other by means of a hinge-type connection (2c) defining a rotation axis ("T") along an edge that is transverse to said longitudinal edge (2d) of said half-shells (2a, 2b), said rotation axis ("T") being perpendicular to said longitudinal axis ("X") along which the casing (2) extends.

24. The control handle (1) according to claim 16, wherein said first half-shell (2a) and said second half-shell (2b) are connected to each other in a respective side connecting portion defining a flexible side connection (2c).

25. The control handle (1) according to claim 16, wherein said driving means (11) comprise a female screw element (12) coupled to a screw member (13), said screw member (13) being fixed onto the respective jaw (9a, 9b) of the respective half-shell (2a, 2b) so as to move said respective jaw (9a, 9b) away from and toward the opposite jaw (9b, 9a).

26. The control handle (1) according to claim 25, wherein said female screw element (12) is rotatably constrained to the respective half-shell (2a, 2b) and at least partially enclosed in the inner part (8a, 8b) of said respective half-shell (2a, 2b) and protrudes externally relative to said respective half-shell (2a, 2b) through at least two openings (14a, 14b) disposed symmetrically on opposite sides of the outer surface of the respective half-shell (2a, 2b).

\* \* \* \* \*